(12) United States Patent
Schmitz et al.

(10) Patent No.: US 9,945,846 B2
(45) Date of Patent: Apr. 17, 2018

(54) DETECTION OF ANTIBODIES USING AN IMPROVED IMMUNE COMPLEX (IC) ELISA

(75) Inventors: Herbert Schmitz, Hamburg (DE); Petra Emmerich-Paloh, Hamburg (DE)

(73) Assignee: BERNHARDT-NOCHT-INSTITUT FUER TROPENMEDIZIN, Hamburg (DE)

( * ) Notice: Subject to any disclaimer, the term of this patent is extended or adjusted under 35 U.S.C. 154(b) by 382 days.

(21) Appl. No.: 14/000,562

(22) PCT Filed: Feb. 21, 2012

(86) PCT No.: PCT/EP2012/052953
§ 371 (c)(1),
(2), (4) Date: Nov. 26, 2013

(87) PCT Pub. No.: WO2012/113801
PCT Pub. Date: Aug. 30, 2012

(65) Prior Publication Data
US 2014/0080120 A1    Mar. 20, 2014

(30) Foreign Application Priority Data
Feb. 22, 2011  (EP) .................................... 11001497

(51) Int. Cl.
| | |
|---|---|
| C07K 16/00 | (2006.01) |
| C07K 16/28 | (2006.01) |
| C12N 15/00 | (2006.01) |
| C12P 21/08 | (2006.01) |
| A61K 38/00 | (2006.01) |
| G01N 33/543 | (2006.01) |
| G01N 33/68 | (2006.01) |

(52) U.S. Cl.
CPC ... *G01N 33/54306* (2013.01); *G01N 33/6854* (2013.01); *G01N 2333/70535* (2013.01)

(58) Field of Classification Search
CPC ............ C07K 2317/732; C07K 16/283; C07K 2317/24; A61K 2039/505
See application file for complete search history.

(56) References Cited

U.S. PATENT DOCUMENTS

| | | | |
|---|---|---|---|
| 5,623,053 A | 4/1997 | Gastinel et al. | |
| 5,985,599 A | 11/1999 | McKenzie et al. | |
| 2002/0048583 A1* | 4/2002 | Schultes ............ | A61K 39/0011 424/153.1 |

FOREIGN PATENT DOCUMENTS

| | | |
|---|---|---|
| CN | 1575184 | 2/2005 |
| CN | 1766621 | 5/2006 |
| CN | 101611052 | 12/2009 |
| EP | 1006183 | 3/1998 |
| WO | WO8911490 | * 11/1989 |
| WO | WO8912231 | * 12/1989 |
| WO | WO9608512 | * 3/1996 |
| WO | WO2008070927 | * 6/2008 |

OTHER PUBLICATIONS

Bruhns et al., Blood, 2009, 113(16):3716-3725.*
Cuzzubbo, et al., "Comparison of PanBio Dengue Duo Enzyme-Linked Immunosorbent . . . " Clinical and Diagnostic Lab. Immunology, Sep. 1999, pp. 705-712.
Hack, et al., "The IgG Detected in the C1q Solid-Phase Immune-Complex Assay . . . " Clinical Immunology and Immunopathology, 1986, pp. 120-128.
Ludolfs, et al., "Reverse ELISA for the detection of anti West Nile virus IgG antibodies in humans" European Journal of Clinical Microbiology, 2007, pp. 467-473.
Greunke, et al., "Recombinant IgY for Improvement of Immunoglobulin based analytical applications" Clinical Biochemistry, 2008, pp. 1237-1244.
Nimmerjahn, et al., "FcY Receptors: Old Friends and New Family Members" Immunity 24, Jan. 2006, pp. 19-28.
Emmerich, et al., "Reverse ELISA for IgG and IgM antibodies to detect Lassa virus infections in Africa" Journal of Clinical Virology 37, 2006, pp. 277-281.
Vazquez, et al., "Evaluation of Immunoglobulin M and G capture enzyme-linked immunosorbent assay . . . " Journal of Clinical Virology 39, 2007, pp. 194-198.
Vance, et al., "Binding of Monomeric Human IgG Defines an Expression Polymorphism . . . " The Journal of Immunology, vol. 51, Dec. 1993, pp. 6429-6439.
Astier, et al., "Human Epidermal Langerhans Cells Secrete a Soluble Receptor for IgG . . . " The American Association of Immunologists, 1994, pp. 201-212.
Duquerroy, et al., "Crystal Structure of a Human Autoimmune Complex between IgM Rheumatoid Factor . . . " Journal of Molecular Biology, 2007, pp. 1321-1331.
Throsby, et al., "Isolation and Characterization of Human Monoclonal Antibodies from Individuals . . . " Journal of Virology, Jul. 2006, pp. 6982-6992.
Sachers, et al., "Simple Detection of Antibodies to Different Viruses using Rheumatoid Factor . . . " Journal of Virological Methods, 1985, pp. 99-110.
Ludolfs, et al., "Highly Specific Detection of Antibodies to tick-borne encephalitis (TBE) virus in humans using . . . " Journal of Clinical Virology, 2009, pp. 125-128.
Bohlson, et al., "Complement proteins C1q and MBL are pattern recognition molecules that signal immediate . . . " Molecular Immunology 44, 2007, pp. 33-43.
Jefferis, et al., "The Specificity and Reactivity of Rheumatoid Factors with Human IgG" Biological Interactions, vol. 26, 1989, pp. 45-60.
Anderson, et al., "Monoclonal Antibodies to Fc Receptors for IgG on Human Mononuclear Phagocytes" The Journal of Biological Chemistry, vol. 261, No. 27, 1986, pp. 12856-12864.
Ravetch, et al., "IgG Fc Receptors" Annual Review of Immunology, 2001, pp. 275-290.

(Continued)

*Primary Examiner* — Barry A Chestnut
(74) *Attorney, Agent, or Firm* — Meunier Carlin & Curfman LLC (57) ABSTRACT

The present invention relates to the field of diagnostic or analytic methods. In particular, the inventors teach that FcγR such as CD16, CD32 or CD64 may be used for in vitro quantification of antibodies in the form of immune complexes, i.e., complexes formed by antigen and specific antibody. A method for detection and quantification of antibodies in the form of immune complexes is also provided.

23 Claims, 2 Drawing Sheets

(56) References Cited

OTHER PUBLICATIONS

Teeling, et al., "Therapeutic efficay of intravenous immunoglobulin preparations depends on the immunoglobulin . . . " Blood, vol. 98, No. 4, Aug. 2001, pp. 1095-1099.
Bruhns, et al., "Specificity and affinity of Human FcY receptors and their polymorphic . . . " Blood, vol. 113, No. 16, Apr. 2009, pp. 3716-3725.
The International Search Report issued by the European Patent Office as International Search Authority for PCT/EP2012/052953 dated Mar. 13, 2012.
The Search Report issued by the State Intellectual Property Office of PRC for corresponding Chinese Patent Application No. 201280009756.1, dated Aug. 2014.

\* cited by examiner

DETECTION OF ANTIBODIES USING AN IMPROVED IMMUNE COMPLEX (IC) ELISA

CROSS REFERENCE TO RELATED APPLICATIONS

The present application is a National Phase Application of International Application No. PCT/EP2012/052953, filed Feb. 21, 2012, which claims priority to European Patent Application No. 11001497.4, filed Feb. 22, 2011, which applications are incorporated herein fully by this reference.

The present invention relates to the field of diagnostic or analytic methods. In particular, the inventors teach that FcγR such as CD16, CD32 or CD64 may be used for in vitro quantification of antibodies in the form of immune complexes, i.e., complexes formed by antigen and specific antibody. A method for detection and quantification of antibodies in the form of immune complexes is also provided.

In various publications, highly sensitive immune complex (IC) ELISAs were described for the detection of IgG antibodies to Cytomegalovirus (Sachers, Emmerich et al. 1985), Lassa virus capsid antigen (Emmerich, Thome-Bolduan et al., 2006) and to type-specific antigens on the surface of West Nile (WN) and Tick borne Encephalitis (TBE) viruses (Ludolfs, Niedrig et al. 2007; Ludolfs, Reinholz et al. 2009). The latter two tests, using the ED3 domain of the respective flaviviruses, did no longer show the inter-flavi cross-reactivity frequently seen using commercially available routine ELISAs or indirect immunofluorescence (IIF). In principle, plates coated with Rheumatoid factor (RF) IgM from patients with Rheumatoid arthritis effectively bind immune complexes (ICs), which form upon mixing of human serum samples containing specific IgG antibodies and the respective peroxidase-labelled antigen (enzyme-labelled antigen, ELA (Sachers, Emmerich et al., 1985).

Compared to antibody assays using antigen coated plates and labelled-anti-human IgG like indirect ELISA or IIF, the IC ELISA has turned out to have several advantages.

By adding the serum samples and the respective ELA, two immunological steps are required for a positive result. The specific antibody has to react with the antigen before the aggregated, i.e., immunocomplexed, IgG antibody binds to the RF IgM on the solid phase. Thus, two immunological mechanisms are involved.

The approach to detection of IC has advantages, in particular, the huge excess of monomeric IgG, which usually causes background reactions using indirect ELISAs or IIF tests, does no longer produce background staining with the IC ELISA, and low serum dilutions of 1:10 can be applied. Due to peroxidase (POD)-labelling, low molecular weight antigens will be aggregated, which fosters the formation of large ICs with many POD molecules. Therefore, high dilutions of the ELAs (usually 1:≥20 000 for the West Nile and TBE ELAs) can be used. This also contributes to the low background staining.

Since the various ELAs can be applied at high dilutions, competitive cross-reacting unlabelled antigens can be added at an excess of about 100-fold (Ludolfs, Reinholz et al. 2009). Thus, the specificity of the IC ELISA for selective epitopes can be increased. Finally, the IC ELISA is technically very simple to perform, since antigen and antibody can be applied simultaneously and only one incubation and washing step is required before the test is stained.

The high specificity of the WN- and TBE-IC ELISAs had already been documented using numerous serum samples of TBE vaccinees and of patients after WN infection. In contrast to IIF or indirect ELISA, where many of these samples showed the well-known cross-reactions, using the TBE samples in the WN IC ELISA, no reactions (P/N<1) were seen. Vice versa, using the samples of WN fever reconvalescents in TBE IC ELISA, no cross-reactivity was observed. (Ludolfs, Niedrig et al. 2007; Ludolfs, Reinholz et al. 2009).

Cross-reactivity of human or animal antibodies to different flaviviruses is a well known phenomenon. Using mouse or even human monoclonal antibodies to the envelope glycoprotein of West Nile, dengue-, or TBE viruses, common flavivirus epitopes have been indentified. For example, 80% of the mouse monoclonal antibodies to West Nile virus or Dengue virus envelope protein were cross-reacting, while only few monoclonals, mostly directed to the ED3 domain of the envelope protein (8%), were specific for the virus in question. The highly immunogenic ED3 is a putative receptor-binding domain, and several neutralizing monoclonal antibodies bind to ED3 of WN or dengue viruses.

Using the ED3 domain as source of antigen, IC ELISAs were much more specific than most routine anti-flavivirus ELISAs or IIF. The POD-labelled ED3 domain protein can be applied at extremely high dilutions (1:20, 000-1:40,000). Thus, it is possible to block unwanted specificities by adding a heterologous ED3 antigen in 100 fold excess (Ludolfs, Reinholz et al. 2009). The high dilutions of the labelled ED3 protein can be explained by the crosslinking of the antigen due to peroxidase labelling, since Biotin-labelling, which does not give rise to aggregation, turned out to be much less effective. In the presence of specific antibodies, very large ICs exceeding 300 000 Da, and containing numerous POD molecules, are formed. Therefore, few labelled ICs bound to the solid phase will be sufficient to produce a strong POD signal. However over night incubation is needed before these large ICs have successively displaced the non-specific IgG molecules that bind to the solid phase coated FcR molecules. This competition between non-specific IgG molecules and ICs may be especially problematic, when much IgG is present in serum samples in aggregated form. Therefore, the storage conditions of the serum samples may influence the sensitivity of the IC ELISA. Storage of undiluted sera at 4° C. or freezing at −20° C. seems to be tolerated, while repeated freezing and thawing cycles or heating (60° C.) seem to increase the proportion of agIgG and may be disadvantageous for optimum sensitivity.

However, some disadvantages in using the IC ELISAs have to be named: A sufficient sensitivity of the assay, i.e. sufficiently high positive to negative ratios, are obtained only after over night incubation. Therefore, in comparison to indirect ELISAs, relatively long incubation times are required for the ICs. On the other hand, especially for epidemiological studies, immediate results are often not required, and the advantages of the IC ELISAs such as simple performance, which greatly facilitates high throughput testing, sufficient sensitivity and the excellent specificity will probably compensate for some minor disadvantages.

Another major drawback of the IC ELISA concerns the standardization of the RF IgM, which is composed of the IgM fraction of sera from various patients with Rheumatoid arthritis. Thus, both the amount of RF IgM and the specificities of the other IgM antibodies present in the IgM fractions vary from batch to batch. Only about 10% of the IgM antibodies in the RF IgM fraction obtained from patients with Rheumatoid arthritis have RF activity, while 90% show non-RF-specific reactions. Thus, using different batches of RF preparations, the ELISAs were difficult to standardize. This may also lead to interference with the ELA applied in the assays. Human monoclonal antibodies specific for RF might be even more effective than total human RF IgM in binding ICs. Therefore they might represent an alternative, even though there may be problems of availability (Duquerroy, Stura et al. 2007).

While some studies on the activity of different, potentially immune complex binding molecules have been performed, it must be kept in mind that most of these assays have been carried out in tissue culture cells with recombinant surface expression, while data on soluble potentially binding molecules bound to a solid phase have been lacking so far.

The inventors therefore addressed the problem of an alternative approach to providing a method for an immune complex ELISA, which would avoid at least part of the disadvantages of the RF coating, in particular, allowing for better standardization.

In comparison to RF, the inventors tested various IgG binding molecules, which in vivo are active to detect and eliminate ICs, for their suitability for the in vitro test. Firstly, they, chose the complement component C1q. Human C1q, the first component of the classical complement pathway, has a molecular weight of about 410-462 kDa. The hexamere globular heads of C1q exclusively bind to the CH2 domain of IgG molecules or the CH3 domain of IgM. C1q must bind to at least two heavy chains in order to alter its conformation and activate C1r and C1s. Its activation follows after binding to immunoglobulins in the form of ICs bound to multivalent antigens. It is also known to bind to a variety of other activating substances, including C-reactive protein, retroviruses, and mitochondria ((Jefferis and Mageed 1989; Bohlson, Fraser et al. 2007; Duquerroy, Stura et al. 2007). It has previously been shown to preferentially bind to preformed immune complexes (Hack and Belmer 1986).

Also, anti-human IgG was tested for coating the solid phase. Although in vivo, anti-human IgG binds to human IgG, and not preferentially to immune complexes, anti-human IgG has sometimes been chosen to detect antigen-specific human IgG antibodies in vitro in the form of immune complexes (e.g., in Dengue assays) (Cuzzubbo, Vaughn et al 1999; Vazquez, Hafner et al. 2007).

As an alternative receptor for the Fc region of IgG, an Fc receptor (FcR) molecule was also tested. FcγRIIA (CD32), was chosen, which, in contrast to C1q, is preferentially found on the surface of PMN (polymorphonuclear leukocytes) in vivo. The complete CD32 with its transmembrane portion functions in the activation of various immune responses (Astier, de la Salle et al. 1994; Ravetch and Bolland 2001; Nimmerjahn and Ravetch 2006; Anderson, Guyre et al., 1986).

Evidently, in vivo, both human C1q and CD32 molecules are in close contact with human immunoglobulin. While in vivo, the activation and signal transduction of these molecules is brought about only upon binding of aggregated IgG in immune complexes (ICs), this does not necessarily mean that they can differentiate between aggregated and non-aggregated IgG under assay conditions in vitro, i.e., that they might be suitable for improving sensitivity and/or reproducibility of an immune complex ELISA. Thus, in addition to RF and anti-IgG antibodies, the inventors tested both C1q and CD32 for their ability to preferentially bind ICs in the presence of high concentrations of IgG in vitro. By coating these various IC binding proteins to a solid phase, the inventors tried to improve the reproducibility, but also the sensitivity of the earlier published IC ELISAs, e.g., for West Nile and TBE viruses.

The problem faced by the inventors is solved by the subject matter of the claims.

In one aspect, the invention provides use of an FcγR for in vitro quantifying antibodies in the form of immune complexes.

The immune complexes comprise an antigen and an antibody specific for said antigen, thus allowing quantification of specific antibodies. The immune complexes may be formed by adding antigen to a sample comprising antibodies. In that case, the antigen preferably is a labelled antigen, e.g., an enzyme labelled antigen (ELA), which allows for easy detection of the immune complexes. The enzyme may be peroxidase, e.g., horseradish peroxidase. Alkaline phosphatase may also be used. Other labelling methods, like biotinylation or labelling with a fluorescent moiety such as FITC, PE or a fluorescent protein, may also be used. Alternatively, the antigen may be unlabeled if it comprises more than one epitope. A second, a labelled antibody, preferably monoclonal, may then be used to detect and quantify the immune complexes. If the label is biotin, detection may be performed by adding an avidin- or streptavidin-labelled enzyme in a further step. Addition of a substrate of the enzyme, as well known in the state of the art, allows for quantification of label, and consequently, of antibody in immune complexed form.

FcγR, in particular, CD32, may also be used for determination or quantification of preformed immune complexes in a sample.

The immune complexes may thus be quantified to determine or to quantify presence of specific antibodies in the sample. The antibodies, which form the immune complexes, will mostly be of the IgG subclass. IgG1, IgG2, IgG3 and/or IgG4 may be detected. However, the inventors surprisingly showed that avian antibodies can also be detected with CD32, i.e., the FcγR is also capable of binding to immune complexes formed by avian IgY antibodies, e.g., chicken IgY. This is unexpected, as IgY does not bind, e.g., to rheumatoid factor.

In the context of the invention, the FcγR may be CD16, CD32 or CD64 or a functional fragment thereof capable of binding to immune complexes. The FcγR preferably is CD32 or a functional fragment thereof capable of binding to immune complexes. CD32 preferably comprises an amino acid sequence having at least 80%, at least 90%, at least 95%, at least 99% or 100% sequence identity with CD32, preferably, human CD32. The fragment of the FcγR preferably comprises an amino acid sequence having at least 80%, at least 90%, at least 95%, at least 99% or 100% sequence identity with the functional FcγR fragment, in particular, human CD32 fragment. The area of the defined sequence identity is capable of binding to immune complexes, e.g., as tested in the examples below. The functional fragment preferably comprises the extracellular part of CD16, CD32 or CD64, in particular, for CD32, FcγRIIA, e.g., FcγRIIAH131. In one embodiment, the FcγR does not comprise a His-Tag, in particular, if the sample may comprise anti-malaria antibodies, which have been shown to be able to cross-react with His-tags under certain conditions.

In one embodiment, CD32 as disclosed by Bruns et al. (2009) is employed in the context of the invention, in particular, CD32 with an amino acid substitution in position 131 (FcγRIIA$_{H131}$ or FcγRIIA$_{R131}$). FcγRIIA$_{V158+\gamma}$ (Bruns et al., 2009) may also be employed.

The IC ELISA experiments with various FcR molecules performed by the inventors show that CD32 is particularly well suited to bind the labelled ICs that form during incubation of serum and ELA.

Other FcγRs like CD16 (FcγR III A or B) are also effective and can thus be used in the method of the invention, however, CD32, especially in the form of FcγRIIAH131, has so far shown the best results. The FcγR, e.g., CD32, is preferably immobilized on a solid support.

The composition comprising antibodies sample that is analysed may be a sample, e.g., a biological sample, such as a sample from a patient. It may also be a sample from a subject known to have, or not to have the antibodies of interest, e.g., as a positive or negative control. Preferably, samples form a subject and a positive and/or negative control are analysed in the same test to allow direct comparison. The sample may be derived from blood (e.g., plasma or, preferably, serum), stool, saliva, or liquor cerebrospinalis. The sample, e.g., serum, may be diluted before contacting the FcγR, e.g., diluted 1:10 or more, e.g., 1:100, in buffer such as PBS or citrate buffer.

The sample may be from a human subject or an animal, e.g., a goat, sheep, horse, cattle, a bird, e.g., chicken, or a rodent such as mouse, rat, rabbit, guinea pig or hamster. The immune complexes may thus be formed by an antigen such as an enzyme-linked antigen and by antibodies which are derived from a species selected from the group comprising human, goat, sheep, horse, cattle, an avian species, e.g., chicken, or a rodent such as mouse, rat, rabbit, guinea pig or hamster. In this context, the FcγR preferably is a human FcγR, as the inventors were able to show that human FcγR, in particular, CD32, has a surprisingly wide interspecies reactivity.

In one embodiment, the immune complexes are formed by addition of antigen to the sample comprising antibodies before contacting the sample with FcγR, i.e., the FcγR binds to preformed immune complexes.

As demonstrated in the examples below, the addition of antigen to the sample comprising antibodies may also be performed in the presence of the FcγR, i.e., the immune complexes may be formed in the presence of the FcγR, e.g., in the presence of CD32. The inventors found that this improves sensitivity of the test in comparison with an embodiment wherein first, the antibodies are bound by the FcγR, and, after a washing step, the antigen is added to form immune complexes. It may also save time in comparison to preformation of immune complexes. The contacting of the FcγR with the antigen may thus be essentially simultaneous with contacting of the FcγR with the composition comprising the antibodies which are to be quantified.

The invention also provides a method for detecting immune complexes, in particular, a method for in vitro quantifying antibodies in the form of immune complexes, comprising
a) coating a solid support with an FcγR under conditions suitable for binding of the FcγR to the solid support,
b) incubating the solid support with a composition comprising an antibody and an antigen, wherein said antibody and said antigen are capable of forming an immune complex, and, and
c) washing the solid support, and then
d) determining quantity of the immune complex.

The solid support may be, e.g., a plastic plate, in particular a plastic plate suitable for ELISA, as well known in the state of the art, e.g., a polystyrene plate having wells, normally, 96 wells. The solid support may also be, e.g., a coverslip, a column or a resin suitable for filling a column, or a bead, e.g., a glass bead, plastic bead, or a magnetic bead. Preferably, the solid support is washed after step a. A blocking step, e.g., with a buffer such as PBS comprising bovine serum albumin (BSA) or another irrelevant protein can also be contemplated.

In one embodiment, the composition of step b comprises an immune complex formed by the antigen and the antibody. The immune complex formed by an antigen and an IgG or IgY antibody may be formed before incubation with the FcγR on the solid support, e.g., by adding an antigen to a sample comprising antibody specific to the antigen. The inventors have shown that a washing step of the solid between incubation of the FcγR with the antibody and incubation with the antigen decreases sensitivity. In comparison, it is better to incubate the FcγR with antigen and antibody simultaneously, i.e., wherein the antigen and antibody have already formed immune complexes, or wherein the immune complexes form in the presence of FcγR. Formation of the immune complex in the presence of FcγR is possible and leads to at least equivalent results. This may save time in comparison with previous formation of the immune complexes. Sufficient incubation times for formation of the complexes and equilibration of binding should be used, as appropriate for the conditions chosen.

Suitable conditions for formation of the immune complexes and binding of the FcγR to the support are described, e.g, in the examples, but are also evident to one of skill in the art. The incubation steps are preferably for one to 48 hours, each. Preferably, the incubation, in particular incubation of the coated support with the antibody and/or immune complexes is carried out for at least 8 hours, at least 12 hours, at least 24 hours, or at least 48 hours, or overnight. In comparison to indirect ELISAs or IIF, relatively long incubation times are thus required for optimal results. One explanation for the finding that the results are better with longer incubation times, might be that the multivalent high molecular ICs need time to compete with and partially displace mIgG or agIgG at the FcγR molecules.

Incubation may be on ice, at 4-8° C. or at room temperature, e.g., at 20° C.-25° C. As will be clear to the skilled person, optimal incubation times and temperatures influence each other, and can be determined according to the needs of the assay and the characteristics of the reagents. Incubation may be in a buffer, e.g., PBS, optionally comprising a non-ionic detergent like Tween and/or a blocking agent such as BSA. Preferably, conditions are chosen, which correspond to conditions in assays known in the state of the art for detecting IC with RF.

Washing steps may, e.g., be carried out with PBS/Tween, optionally comprising BSA or another protein different from the antigen or the antibody. The quantity, presence or absence of the immune complex may be determined as known in the state of the art, e.g., as described for an enzyme-linked antigen in the examples below. Alternatively, a labelled antibody directed to the antigen may be employed for detection. The quantity of label detected correlates with the quantity of antibody in the form of immune complexes, i.e., antibody specific for the antigen.

The antibody may be of IgG or IgY class. In one embodiment of the invention, the antibody is an IgY antibody and the FcγR is CD32. In another embodiment, the antibody is an IgG antibody and the FcγR is CD32.

Further details have been described above with regard to the use of the FcγR, which details also form preferred embodiments in the method of the invention.

The invention also provides a method for diagnosing an infection with a pathogen in a subject, e.g., a virus infection, wherein the method for detecting immune complexes described above is carried out, wherein the composition comprising an antibody is a sample from the subject, and wherein the antigen which can be specifically bound by said antibody is an antigen derivable from the pathogen. The pathogen may, e.g., be a virus, such as West Nile (WN) virus, dengue virus or Tick-borne encephalitis (TBE) virus. The antigen preferably is a surface protein or a surface glycoprotein or a poly- or oligosaccharide structure thereof, such as an envelope protein of a virus. The antigen may be recombinantly prepared. As described before, the antigen may be labelled, e.g. with biotin or an enzyme such as horseradish peroxidase, to facilitate detection. If the subject is a mammal, e.g., a human, the antibody will be an IgG antibody.

Using a sample having a known concentration of antibody as a standard, the amount of antibody in the sample can easily be determined by the skilled person. The amount of antibody can then be compared, e.g., with known amounts of healthy subjects, of subjects having an acute infection with the pathogen or subjects having had an infection with the pathogen in their past. Presence of an antibody specific to an antigen derived from a pathogen typically indicates that the subject is infected with the pathogen or has been infected with the pathogen. As only IgG or the avian homologues thereof are detected, but not IgM, which is formed in the beginning of a first infection with a pathogen, presence of the immune complexes indicates that a class switch has already taken place. A similar amount of antibody may e.g. indicate a similar stage of the infection. The concentration of antibodies in one subject may also be followed over time, which may allow conclusions regarding the course of the infection, or the level of immunity after a vaccination.

The invention provides several advantages over the state of the art. In contrast to RF with its difficulties of standardisation and varying quality, recombinant FcγR are available. Recombinant CD32 is a well-defined commercially available molecule, with similar or even better binding capacities than RF IgM. One further advantage of CD32 rests on the unexpected observation, that, to a certain extent, animal, especially rodent and avian ICs, can also be detected.

The invention is illustrated, but not limited by the specific examples below. All cited literature is herewith incorporated by reference.

EXAMPLES

Material and Methods
Serum Samples:

The source of the human serum samples with or without antibodies to WN and TBE viruses had been presented previously ((Ludolfs, Niedrig et al. 2007; Ludolfs, Reinholz et al. 2009)). Two human sera obtained from patients recovering from West Nile fever and three human sera collected from healthy subjects after TBE vaccination were selected from these earlier studies. 10 sera without anti-TBE and anti-WN antibodies, as documented by indirect immunofluorescence (IIF), were obtained from healthy German blood donors. Moreover, a human WN monoclonal directed to the ED3 domain of WN virus (clone 4384) (Throsby, Geuijen et al. 2006), and two rabbit and two chicken sera immunized with WN virus were also included in the study.

Coating with Various Fc-Receptor (FcR) Proteins:

A pool of 100 ml RF (1 mg/ml) was isolated as IgM fraction obtained from numerous human donors (Medac, Hamburg, Germany) and was kept frozen at −70° C. until use. Lyophilized human complement component C1q isolated from human serum (C1q) was obtained from Sigma-Aldrich (Hamburg, Germany). Lyophilized recombinant human soluble FcγRIIA (CD32) was bought from R&D Systems, Wiesbaden-Nordenstadt, Germany, or alternatively from Sinobiological, Beijing, China. CD16b (human Fcγ RIIIB) was obtained from R&D Systems. Affinity purified anti-human IgG was obtained from Medac, Hamburg, Germany. All materials were diluted to a concentration of 8 μg/ml in PBS+0.1% $NaN_3$ and were added to Maxisorb microtiter strips (60 μl/well, Nunc, Copenhagen, Denmark). After incubation for at least 48 h at 4° C., the wells were overlaid with 50 μl mineral oil (Sigma-Aldrich, Hamburg) and sealed with adhesive tap. The strips could be stored at 4° C. for at least one month. After lyophilisation, in vacuum bags, they were stable for at least one year.

IC ELISA for IgG Antibodies to TBEV and to WNV

The IC ELISA started with three rounds of washing of the microtiter strips with phosphate buffered saline (pH 7.5) containing 0.05% Tween 20 (PBST). Due to the high dilutions of the ELA in the presence of BSA, the usual blocking of the plates with BSA was not necessary. Serum samples were diluted 1:10 in PBS+ 0.05% ProCline 300 (Sigma-Aldrich, Hamburg). In the presence of peroxidase, $NaN_3$ should not be applied. To each well, 25 μl serum dilution and 25 μl ELA (diluted 1:20 000 in PBST containing 1% BSA, 1% FCS) were added, and the mixture was incubated for 24 h at 4° C. Finally, after renewed washing, the test was stained with TMB (3,3',5,5'-tetramethylbenzidine), stopped with 1N $H_2SO_4$ and read at 450 nm.

The cut-off extinction of the IC ELISA was calculated as the mean extinction of 20 negative sera plus 3 standard deviations. To calculate positive/negative (P/N) ratios, a weak positive serum sample was diluted in 10% negative serum until the cut-off extinction (0.07-0.1) was obtained. With each assay, the extinction (OD450) of all serum samples was divided by the extinction of this cut-off control.

Indirect Immunofluorecence Assay (IIF)

Aceton fixed Vero E6 cells infected with both TBE and WN viruses were used. Sera were tested starting at a dilution of 1:10. Anti-IgG FITC (anti-human-, anti-chicken-, and anti-rabbit-IgG, goat origin, Medac, Hamburg, Germany) was applied at a dilution of 1:100 in PBS containing Trypan blue to counterstain the cells.

IgG Binding

Monomeric IgG (mIgG) was obtained from fresh human serum of healthy blood donors without antibodies to WN or TBE viruses by gel chromatography (Sephacryl 200, GE Healthcare Europe Freiburg, Germany). The purified monomeric IgG (2 mg/ml) was biotinylated using sulfo-NHS-Biotin (Sigma-Aldrich, Hamburg, Germany). The biotinylated monomeric IgG (mIgG) at amounts of 1-0.01 ng/well (in 50 µl) was added to microtiter strips coated with the different FcR binding proteins. Alternatively, the strips were coated with biotinylated heat-aggregated (1 h; 61° C.) IgG (agIgG) (1-100 ng/well). After incubation over night or for 48 hours, the strips were washed, and the bound mIgG was detected using Streptavidin-Peroxidase (Sigma-Aldrich). After incubation for 1 hour and washing, the tests were stained with TMB, stopped with 1N $H_2SO_4$ and read at 450 nm. After 48 hours incubation, the mIgG or agIgG is completely bound to the wells. 1, 2, 3, 4, 5 ng biotinylated mIgG or agIgG, completely bound to uncoated wells upon incubation at 4° C. for 48 hours resulted in OD 450 of 0.21, 0.43, 0.6, 0.77 and 1.01, respectively. This shows that the relationship is linear, and that quantification is possible.

Results:

The principle of the IC ELISA relies on the selective binding of ICs, forming upon mixing of serum samples and ELA, to immobilized FcR molecules. Optimally, the huge excess of monomeric IgG should not be bound. To measure this selective activity of the different FcRs, the inventors took advantage of the fact that biotinylated aggregated IgG (agIgG) can be used as a substitute for ICs (Vance, Huizinga et al, 1993; Teeling, Jansen-Hendriks et al., 2001).

Figure 1:
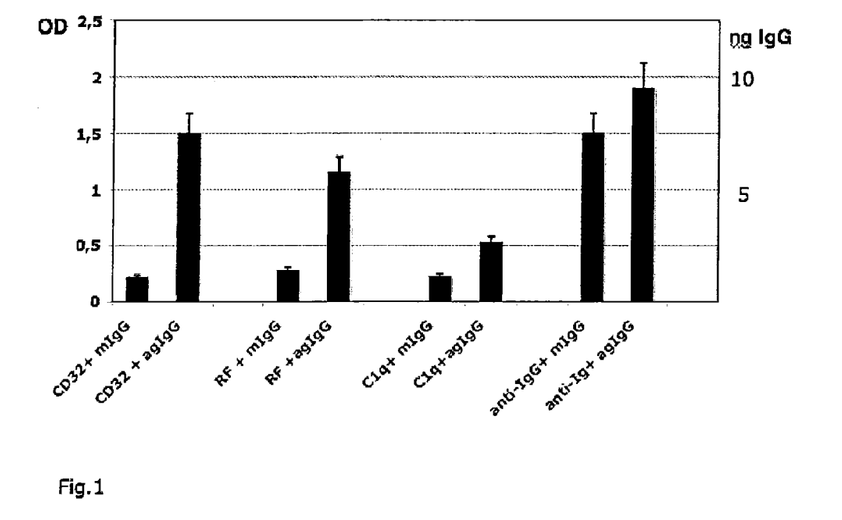
FIG. 1: 50 ng of each biotinylated monomeric IgG (mIgG) and aggregated IgG (agIgG) were added to microtiter strips coated with CD32, RF, C1q and anti-human IgG. After 24 h at 4° C., Streptavidin-POD was added and the amount of bound mIgG and agIgG was measured (1 ng biotinylated mIgG or agIgG is equivalent to an OD 450 of 1.0±10%).

As can be taken from FIG. 1, coating with anti-human IgG (anti-IgG) showed the highest binding capacity for both agIgG and mIgG. However, the proportion of bound agIgG/mIgG was rather low. Surprisingly, the FcR CD32FcRs bound agIgG considerably better than all other molecules tested, even better than the positive control from the state of the art, RF. The selective binding of agIgG was 1.2 fold for monomeric IgG (mIgG), 3 fold for C1q, 4 fold for RF and 11 fold for CD32).

Next, the differently coated solid phase microtiter strips were tested using the IC ELISAs for anti-TBE IgG and anti-WN IgG antibodies. By using the TBE IC ELISA on differently coated microtiter strips (FIG. 2), the P/N ratios obtained with a strong positive (++) and a weak positive (+) sample, both diluted 1:10 are shown. By IIF, the samples had anti-TBE antibody titers of 1:2560, and 1:160, respectively. Moreover, 10 negative control samples (dilution 1:10), a cut-off sample (P/N ratio 1, not shown in the figure) and a buffer control (no serum) were included. Very low background reactions with the negative sample on RF-, C1q- and CD32 coated strips all with a P/N ratio of <1. Also, 9 additional negative samples obtained from German blood donors without TBE vaccination had a P/N ratio of <1. Remarkably, almost no reaction was seen on empty, unblocked strips (no coating, FIG. 2). The low background noise of the TBE ELA can be explained by the high dilution 1:20,000 in the presence of 1% BSA. The two positive samples produced the highest P/N ratios on the CD32 strips. To get some information on the interference of non-specific human IgG, the weak positive sample (+), which had an antibody titer of 1:80 by IIF, was diluted in 10% negative serum. At a dilution of 1:40, the cut-off level (P/N=1) was reached using RF-coated or CD32-coated strips, while with C1q-coating, a completely negative result was already obtained at a dilution of 1:10.

Figure 2:
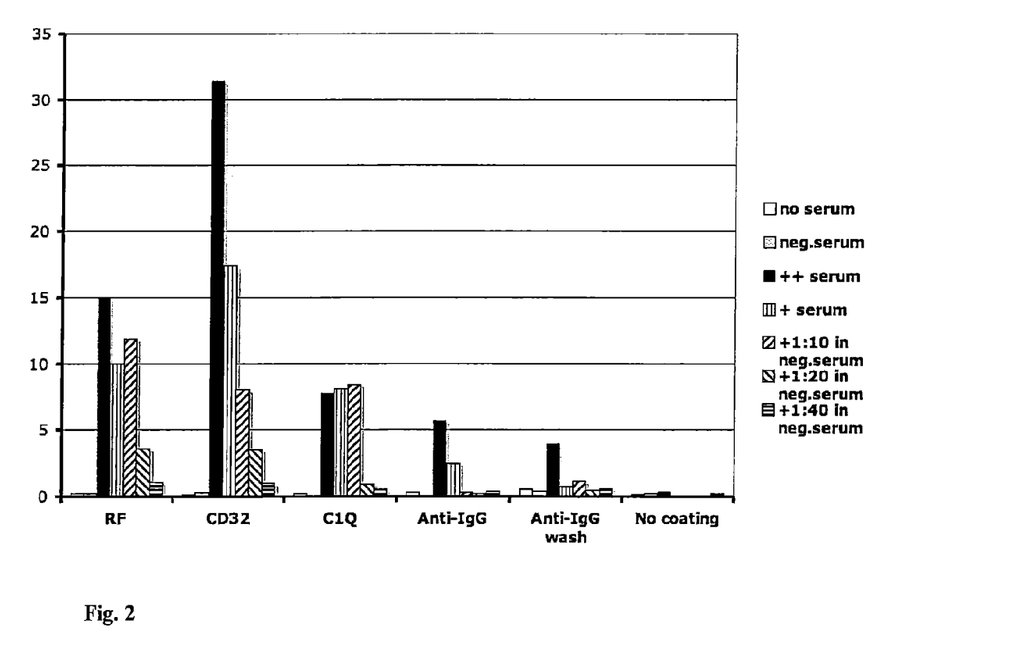
FIG. 2: Three control sera (++ serum; + serum and neg. serum) and the + serum diluted 1:10, 1:20 and 1:40 in 10% negative (neg.) serum were tested on plates coated with RF, CD32, C1q and anti-IgG antibody with intermediated washing (anti-IgG wash) and without (anti-IgG). Due to the high dilution of the ELA (1:20 000) almost no reaction was seen on the empty microtiter plate (no coating).

In addition, the FcR coating was compared with the ability of anti-human IgG-coated strips to detect ICs (FIG. 2, right columns). Here, two different test procedures were compared: on one strip (designated with anti-IgG), the serum and TBE-ELA was applied simultaneously as usual, while on a parallel strip after an incubation of the serum samples of one hour, the strip was washed (Anti-IgG wash), and subsequently the TBE-ELA was applied over night. Interestingly, the reaction of the positive serum was clearly stronger without washing away unbound IgG antibody compared to the procedure with additional washing (P/N ratio 6 and 4 respectively). The latter procedure (with wash) is routinely applied for IgG antibody detection to dengue virus or with anti-µ antibody assays for specific IgM detection. The inventors have thus shown that, in contrast to prior practice, it improves sensitivity if, in an ELISA wherein a labelled, e.g., enzyme-linked antigen is detected, both specific antibody (or serum containing the same) and labeled antigen are incubated simultaneously with a solid support coated with the antibody-binding anti-IgG (Cuzzubbo, Vaughn et al 1999; Vazquez, Hafner et al. 2007).

As shown in FIG. 2, the addition of negative serum to a positive serum interferes with the sensitivity of the TBE ELISA.

To study this phenomenon in more detail, a human monoclonal antibody (hMAB) directed to the ED3 domain of WN virus (clone 4384; originally one mg/ml, IIF antibody titer 1:20,000)) (Throsby, Geuijen, 2006) was applied at different concentrations using the WN IC ELISA together with CD32 coated strips.

Figure 3:
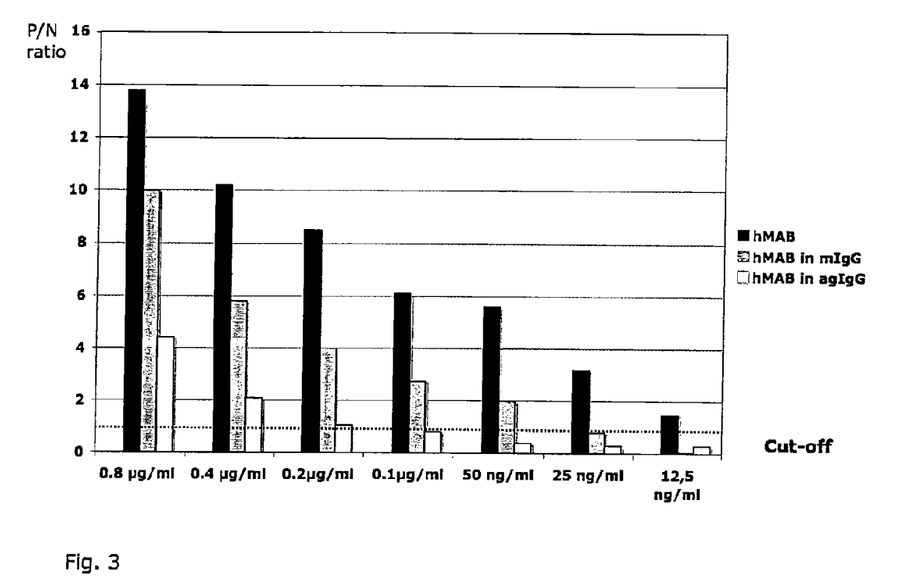
FIG. 3: Using the WN IC and CD32 coating, different concentrations (0.8 μg-12.5 ng/ml) of human monoclonal antibody 4384 were tested, diluted in PBS, in WN negative mIgG (1 mg/ml) and in agIgG (1 mg/ml).

When the hMAB was diluted in PBS, the WN IC ELISA was able to detect very low concentrations thereof, down to 12.5 ng/ml (FIG. 3). However, in the presence of physiological concentrations of mIgG (1.5 mg/ml), which are usually found in serum samples diluted corresponding to a serum dilution of 1:10, only 50 ng/ml could be detected. The strongest effect was shown by agIgG, which clearly reduced the analytic sensitivity of the WN IC ELISA to 0.4 µg/ml. Obviously, agIgG, and to a lesser extent, mIgG hinders the labelled ICs from binding to the CD32-coated strips.

Figure 4:
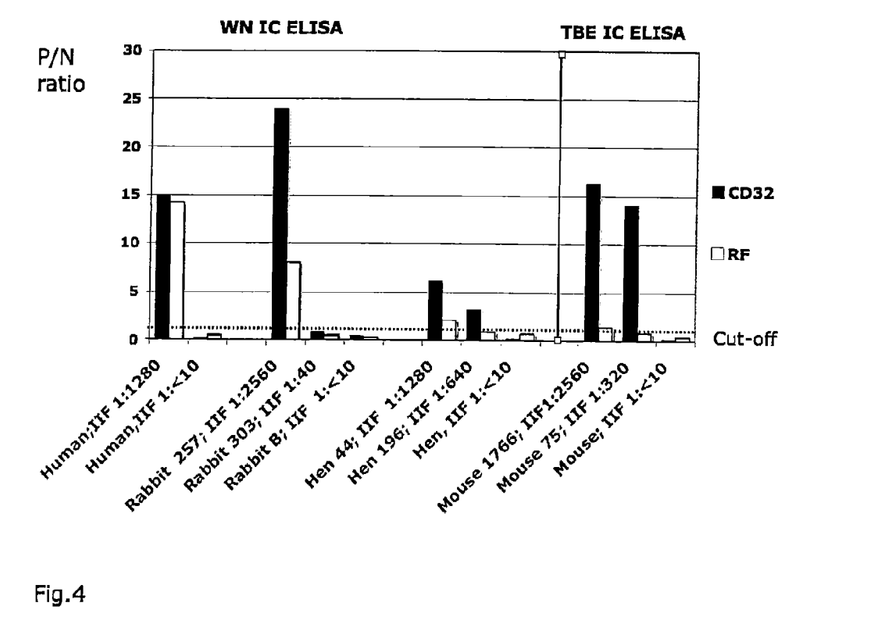
FIG. 4: Sera of immunized rabbits and chicken were tested for anti-WN antibodies using the WN IC ELISA and strips coated both with CD32 and RF.

Further, the reactivity of samples of various animals immunized with either WN or TBE virus was tested (FIG. 4). The rabbit and chicken sera with high IIF antibody titers to WN virus produced P/N ratios between 24 and 1, using the WN IC ELISA and CD32 coated strips. The RF coating (open columns) was clearly less sensitive. Similarly, using the TBE IC ELISA and two mouse MABs directed to the ED3 domain of TBE, positive reactions were seen only on CD32 coated strips. Again the RF coating resulted in very low or even negative P/N ratios also for the mouse samples. Thus, CD32 coated strips, showing a considerably stronger interspecies IgG cross-reactivity for IgG than RF, might be suitable for detecting antibodies not only of human but also of rodent or even of avian origin.

DISCUSSION

Several low affinity FcγR molecules are preferentially activated by agIgG compared to mIgG in vivo or in tissue culture (Bruhns, Iannascoli et al. 2009) The inventors therefore tested the coating of the solid phase strips various agIgG-binding molecules using both biotinylated mIgG and agIgG. Thus, suitable capturing molecules for the IC ELISA could be tested. In first experiments, the measurement of the selective binding capacity of agIgG was substituted for selective binding capacity of ICs. The experiments were then confirmed by analysing binding capacity of ICs.

In the case of RF, binding to epitopes on the Fc-portion of IgG, which are only exposed after antigen binding, might play a role in preferential binding of immune complexes (Hack and Belmer 1986; Bohlson, Fraser et al. 2007; Duquerroy, Stura et al. 2007). In in vivo experiments, previous results that cells such as macrophages contacted with IC showed a stronger activation could also be attributed to spatial effects on the cell membrane induced by clustering of receptors. Such effects cannot play a role in in vitro assays such as in the method of the invention. It is also so far unclear why, compared to RF, in the FcγR, in particular CD32, the selectivity of in vitro binding is even stronger.

Surprisingly, CD32 was able to preferentially bind agIgG but to much higher extent than C1q, RF or anti-human IgG.

The IC ELISAs for antibodies to TBE and WN are sufficiently sensitive for most practical purposes, e.g., for diagnosis of the presence of antibodies against pathogens such as viruses. Even low IIF antibody titers and down to 50 ng of specific MAB were detected. In comparing sensitivity of the IC ELISA with IIF, it must be kept in mind that the IC ELISA uses only a small antigen (ED3 domain) with only 5-6 epitopes (Throsby, Geuijen et al. 2006; Sukupolvi-Petty, Austin et al. 2007), while in IIF, only on the E protein, 20-30 epitopes are exposed.

LITERATURE

Anderson, C. L., P. M. Guyre, et al. (1986). "Monoclonal antibodies to Fc receptors for IgG on human mononuclear phagocytes. Antibody characterization and induction of superoxide production in a monocyte cell line." *J Biol Chem* 261(27): 12856-64.

Astier, A., H. de la Salle, et al. (1994). "Human epidermal Langerhans cells secrete a soluble receptor for IgG (Fc gamma RII/CD32) that inhibits the binding of immune complexes to Fc gamma R+ cells." *J Immunol* 152(1): 201-12.

Bohlson, S. S., D. A. Fraser, et al. (2007). "Complement proteins C1q and MBL are pattern recognition molecules that signal immediate and long-term protective immune functions." *Mol Immunol* 44(1-3): 33-43.

Bruhns, P., B. Iannascoli, et al. (2009). "Specificity and affinity of human Fcgamma receptors and their polymorphic variants for human IgG subclasses." *Blood* 113(16): 3716-25.

Cuzzubbo A J; D. W. Vaughn (1999). "Comparison of PanBio dengue duo enzyme-linked immunosorbent assay (ELISA) and MRL dengue fever virus immunoglobulin M capture ELISA for diagnosis of dengue virus infections in Southeast Asia" *Clinical and diagnostic laboratory immunology* 6(5):705-12.

Duquerroy, S., E. A. Stura, et al. (2007). "Crystal structure of a human autoimmune complex between IgM rheumatoid factor RF61 and IgG1 Fc reveals a novel epitope and evidence for affinity maturation." *J Mol Biol* 368(5): 1321-31.

Emmerich, P., C. Thome-Bolduan, et al. (2006). "Reverse ELISA for IgG and IgM antibodies to detect Lassa virus infections in Africa." *J Clin Virol* 37(4): 277-81.

Hack, C. E. and A. J. Belmer (1986). "The IgG detected in the C1q solid-phase immune-complex assay is not always of immune-complex nature." *Clin Immunol Immunopathol* 38(1): 120-8.

Jefferis, R. and R. A. Mageed (1989). "The specificity and reactivity of rheumatoid factors with human IgG." *Monogr Allergy* 26: 45-60.

Ludolfs, D., M. Niedrig, et al. (2007). "Reverse ELISA for the detection of anti West Nile virus IgG antibodies in humans." *Eur J Clin Microbiol Infect Dis* 26(7): 467-73.

Ludolfs, D., M. Reinholz, et al. (2009). "Highly specific detection of antibodies to tick-borne encephalitis (TBE) virus in humans using a domain III antigen and a sensitive immune complex (IC) ELISA." *J Clin Virol* 45(2): 125-8.

Nimmerjahn, F. and J. V. Ravetch (2006). "Fcgamma receptors: old friends and new family members." *Immunity* 24(1): 19-28.

Ravetch, J. V. and S. Bolland (2001). "IgG Fc receptors." *Annu Rev Immunol* 19: 275-90.

Sachers, M., P. Emmerich, et al. (1985). "Simple detection of antibodies to different viruses using rheumatoid factor and enzyme-labelled antigen (ELA)." *J Virol Methods* 10(2): 99-110.

Teeling, J. L., T. Jansen-Hendriks, et al. (2001). "Therapeutic efficacy of intravenous immunoglobulin preparations depends on the immunoglobulin G dimers: studies in experimental immune thrombocytopenia." *Blood* 98(4): 1095-9.

Throsby, M., C. Geuijen, et al. (2006). "Isolation and characterization of human monoclonal antibodies from individuals infected with West Nile Virus." *J Virol* 80(14): 6982-92.

Vance, B. A., T. W. Huizinga, et al. (1993). "Binding of monomeric human IgG defines an expression polymorphism of Fc gamma RIII on large granular lymphocyte/natural killer cells." *J Immunol* 151(11): 6429-39.

Vasquez, Hafner et al. (2007). "Evaluation of immunoglobulin M and G capture enzyme-linked immunosorbent assay Panbio kits for diagnostic dengue infections". *J Clin Virol*. 39(3):194-8.

The invention claimed is:

1. A method for in vitro quantifying antibodies in a sample, comprising
    a) adding an antigen to the sample comprising antibodies, thereby forming immune complexes;
    b) contacting the immune complexes with an isolated FcγR; and
    c) quantifying the antibodies in the form of immune complexes, wherein the isolated FcγR is selected from the group consisting of CD32 and CD64.

2. The method of claim 1, wherein the addition of antigen to the sample is performed in the presence of isolated FcγR.

3. The method of claim 1, wherein the addition of antigen to the sample is performed before contacting the sample and antigen with isolated FcγR.

4. The method of claim 2, wherein the antigen is a labeled antigen selected from the group consisting of an enzyme labeled antigen and a biotin labeled antigen.

5. The method of claim 1, wherein the antibodies are derived from a biological sample.

6. The method of claim 1, wherein the antibodies are derived from a species selected from the group consisting of human, goat, sheep, horse, cattle, bird, and rodent.

7. The method of claim 1, wherein the antibodies are IgG or IgY antibodies.

8. The method of claim 1, wherein the isolated FcγR is CD32 or a functional fragment thereof capable of binding to immune complexes.

9. The method of claim 8, wherein CD32 or the functional fragment thereof comprises the extracellular part of CD32.

10. A method for in vitro quantifying antibodies in the form of immune complexes, comprising
    a) adding an antigen to a sample comprising IgG or IgY antibodies, thereby forming immune complexes b) coating a solid support with an isolated FcγR under conditions suitable for binding of the isolated FcγR to the solid support, c) incubating the solid support with a composition comprising said immune complexes, and d) washing the solid support, and then e) determining the quantity of the bound immune complexes, wherein the isolated FcγR is selected from the group consisting of CD32 and CD64.

11. The method of claim 10, wherein the immune complexes are formed in the presence of the isolated FcγR.

12. The method of claim 10, wherein the antigen is a labelled antigen selected from the group consisting of an enzyme labelled antigen and a biotin labelled antigen.

13. The method of any of claim 10, wherein the isolated FcγR is CD32 or a functional fragment thereof capable of binding to immune complexes.

14. A method for diagnosing infection with a pathogen in a subject, wherein the method of claim 10 is carried out, wherein the sample comprises IgG antibodies, and wherein the antigen which can be specifically bound by said IgG antibody is an antigen derivable from the pathogen.

15. A method of diagnosing an infection with a pathogen in a subject comprising obtaining a biological sample from the subject and quantifying the antibodies in the sample according to claim 1.

16. The method of claim 6, wherein the antibodies are derived from a bird; and wherein the bird is a chicken.

17. The method of claim 6, wherein the antibodies are derived from a rodent; and wherein the rodent is a mouse, rat, rabbit, guinea pig, or hamster.

18. The method of claim 14, wherein the antigen is an envelope protein of a virus.

19. The method of claim 9, wherein the CD32 is FcγRIIAH131.

20. The method of claim 9, wherein the CD32 is FcγRIIAR131.

21. The method of claim 9, wherein the CD32 is FcγRIIAV158γ.

22. A method for in vitro quantifying antibodies in a sample, comprising a) adding an antigen to the sample comprising antibodies, thereby forming immune complexes;

b) contacting the immune complexes with soluble FcγR; and c) quantifying the antibodies in the form of immune complexes, wherein the isolated FcγR is selected from the group consisting of CD32 and CD64.

23. The method of claim 1 or claim 10, wherein the solid support is selected from a group consisting of a plastic plate, a coverslip, a column or a resin suitable for filling a column and a bead.

* * * * *